United States Patent [19]
Yates, III

[11] Patent Number: 5,765,739
[45] Date of Patent: Jun. 16, 1998

[54] DENTAL FLOSS DISPENSER

[76] Inventor: Russell Yates, III, 1020 Grand Concourse, Apt. 17E, Bronx, N.Y. 10451

[21] Appl. No.: 786,779

[22] Filed: Jan. 21, 1997

Related U.S. Application Data

[63] Continuation-in-part of Ser. No. 415,527, Apr. 3, 1995, abandoned.

[51] Int. Cl.⁶ .................................................. A61C 15/04
[52] U.S. Cl. .............................. 225/23; 132/323; 225/77
[58] Field of Search ........................... 225/23, 16, 77; 83/436.5, 436.55, 649, 950; 206/39.8; 132/327

[56] References Cited

U.S. PATENT DOCUMENTS

| | | | |
|---|---|---|---|
| 495,892 | 4/1893 | Keep | 83/436.5 |
| 2,021,038 | 11/1935 | West | 83/649 |
| 2,206,979 | 7/1940 | Steiner | 225/23 |
| 2,334,757 | 11/1943 | Ensminger | 225/23 |
| 2,761,503 | 9/1956 | Krueger | 83/649 |
| 5,020,554 | 6/1991 | Feinberg | 132/323 |

*Primary Examiner*—Kenneth E. Peterson
*Attorney, Agent, or Firm*—Charles E. Temko

[57] ABSTRACT

A wall mounted dental floss dispenser is disclosed. The dispenser includes a mounting bracket supporting a housing. Within the housing is a vertically oriented plate having a recess for supporting a known replaceable pocket floss dispenser. Floss is guided downwardly to be engaged by a pair of nip rollers, one of which is manually rotated to advance the floss to an outlet opening in said housing adjacent a cutting blade. Use of the device enables the obtaining of a desired length of floss using only a single hand of the user.

3 Claims, 4 Drawing Sheets

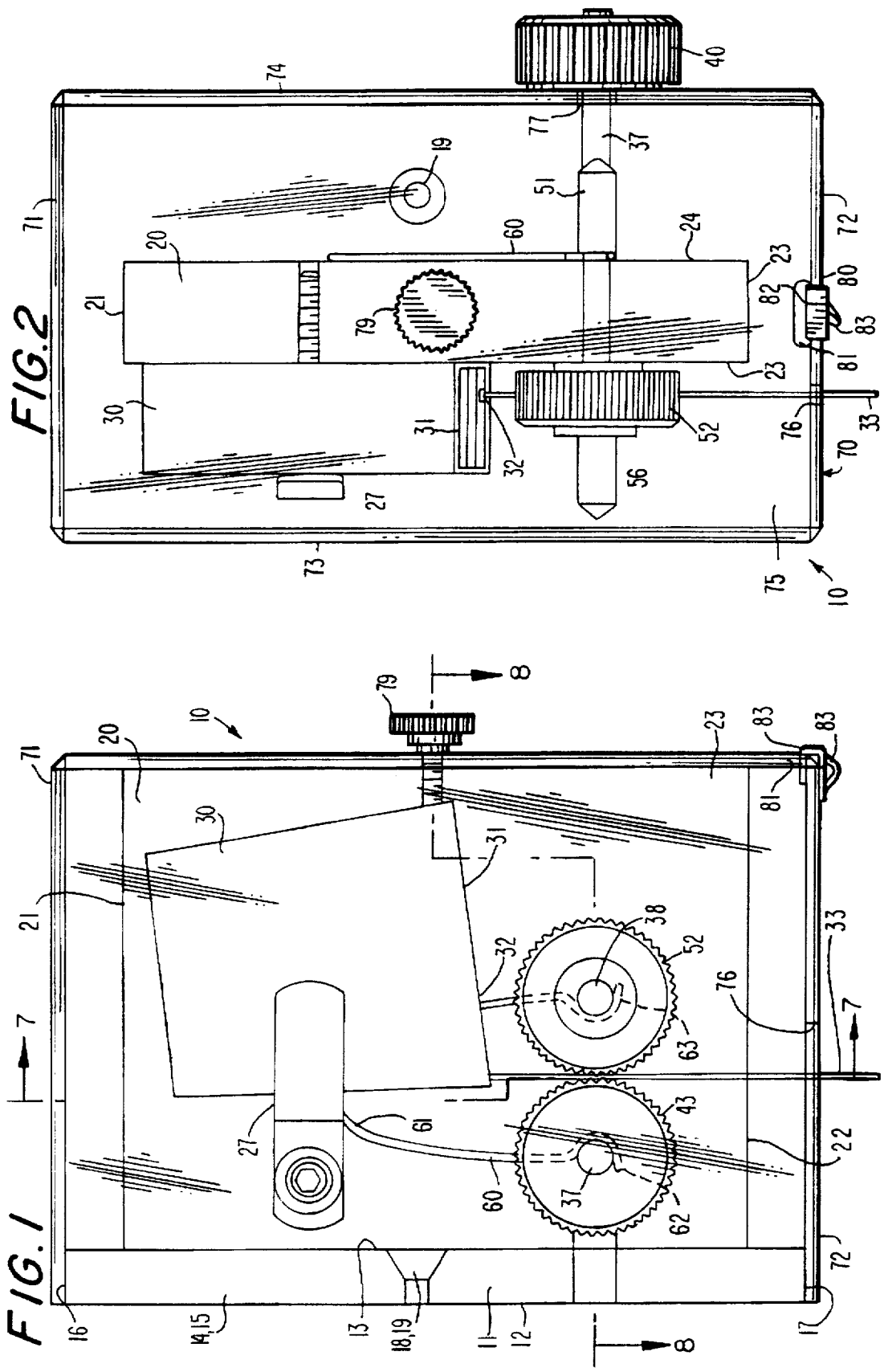

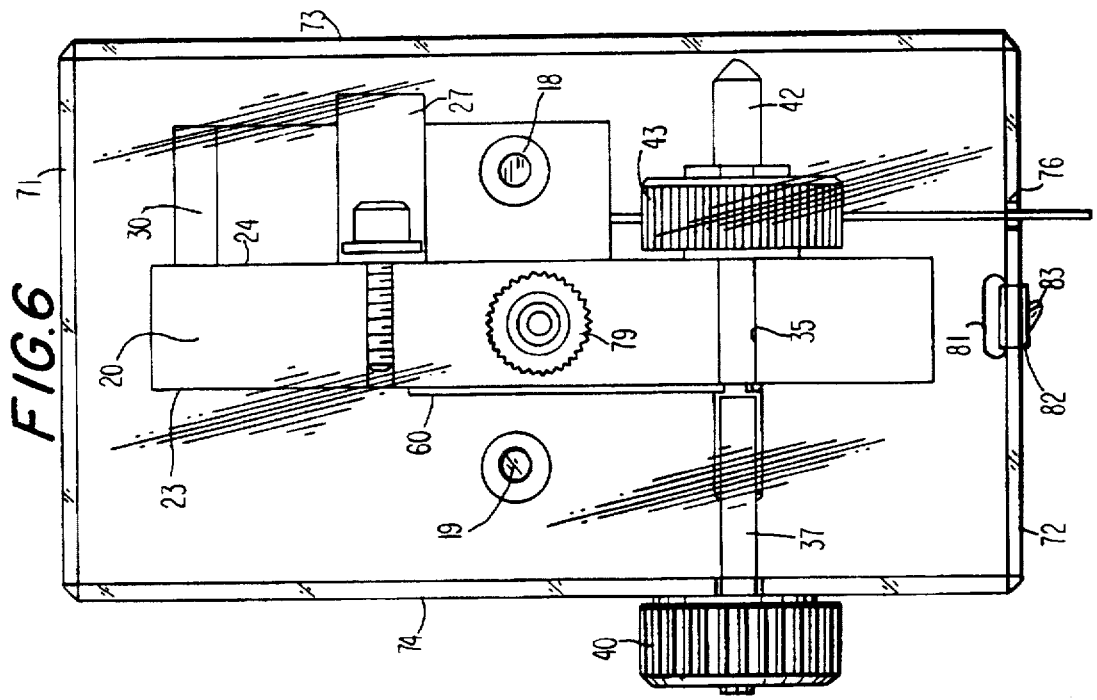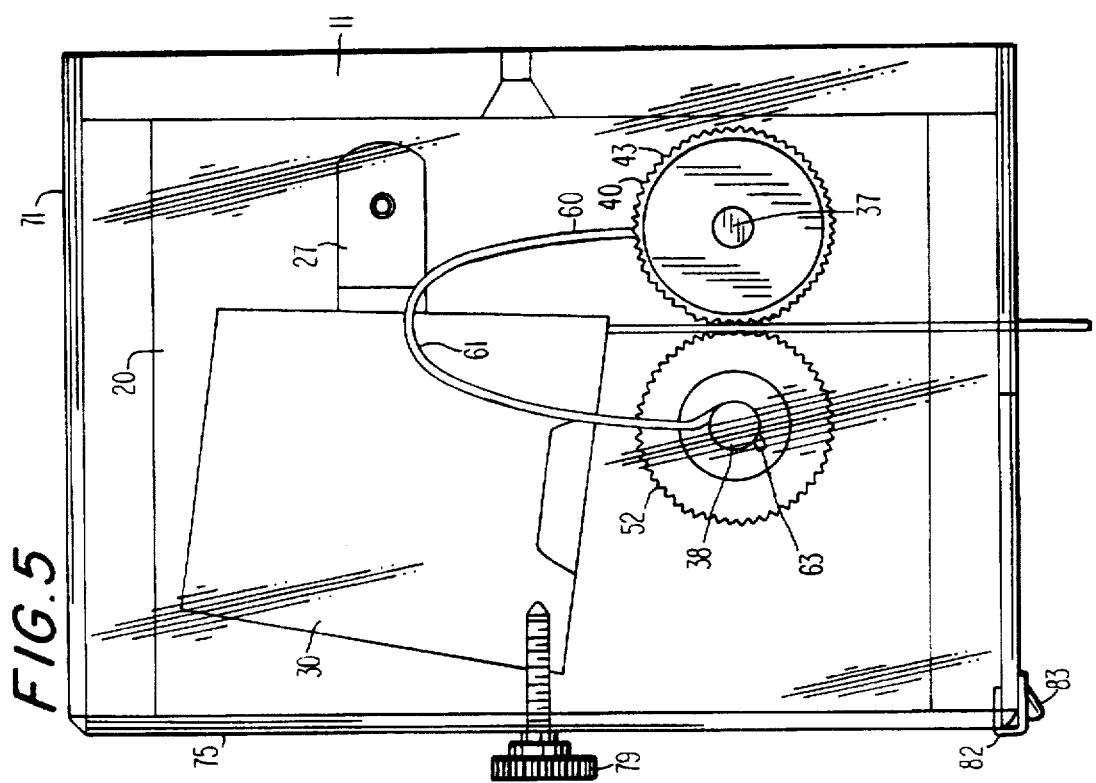

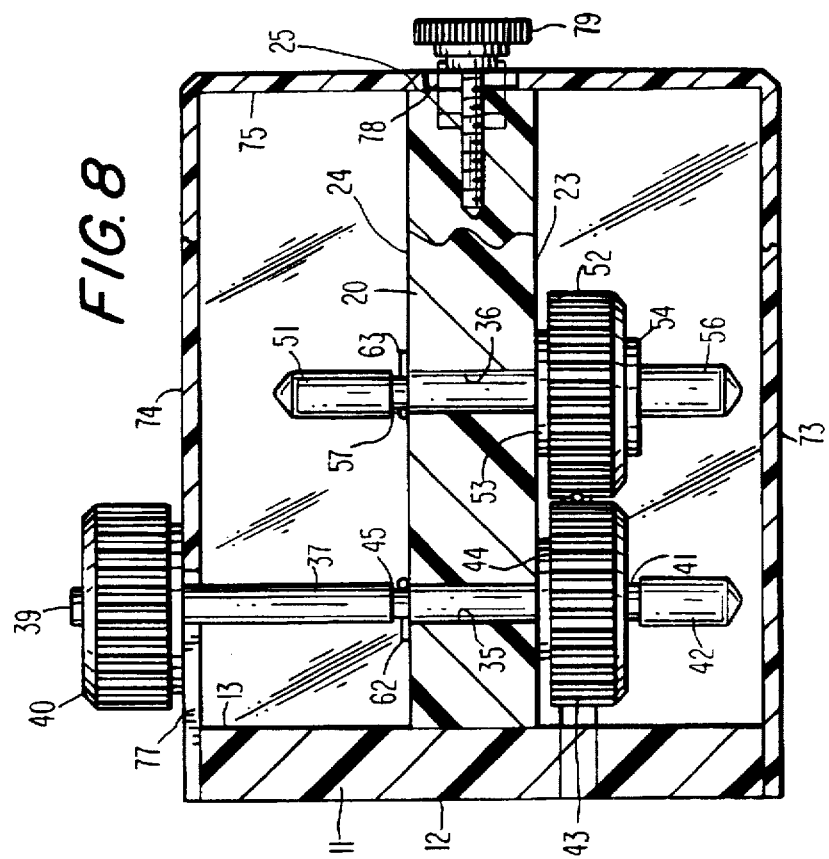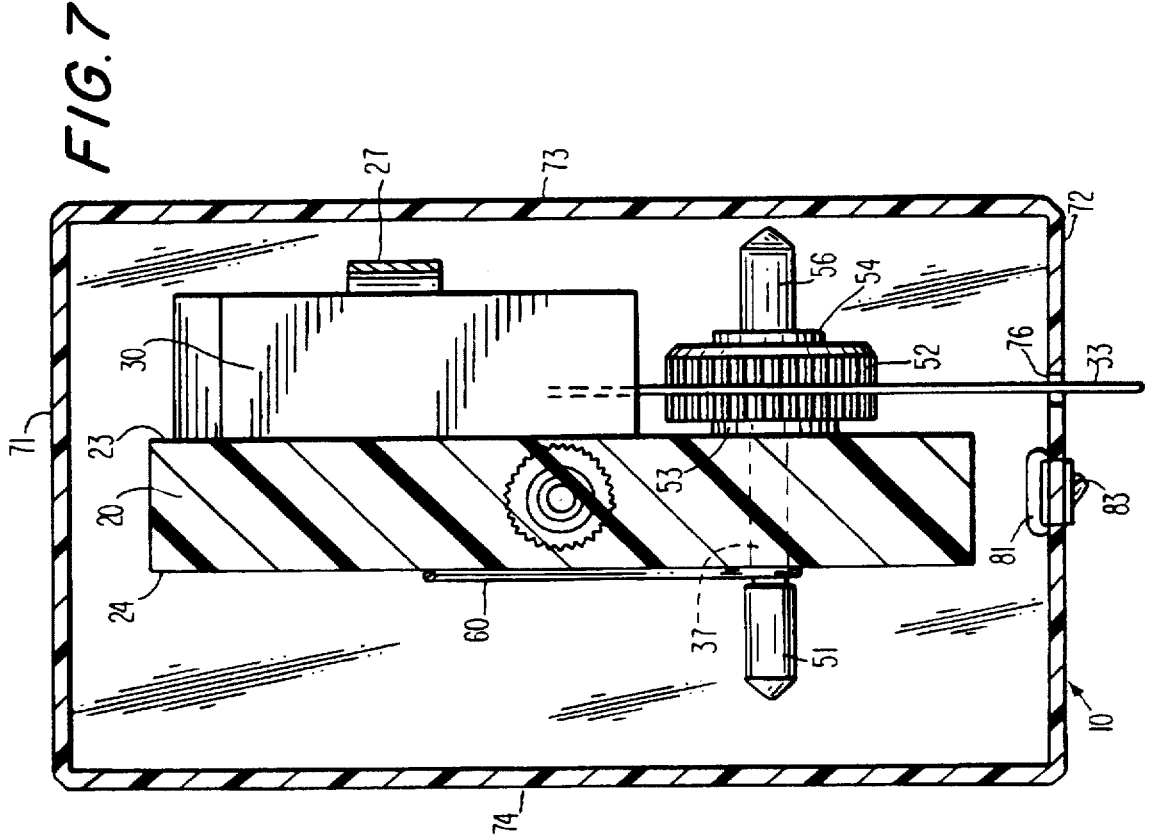

DENTAL FLOSS DISPENSER

RELATED APPLICATION

This application is a continuation-in-part of my application Ser. No. 08/415,527 filed Apr. 3, 1995, now abandoned, under the title Dental Floss Dispenser.

BACKGROUND OF THE INVENTION

This invention relates generally to the field of dispensing devices, and more particularly to an improved wall mounted device for dispensing dental floss which is conveniently positioned adjacent a sink in a bathroom or similar location. Devices of this general type are known in the art, and the invention lies in specific constructional details which afford improved ease of operation and utility, as well as convenience in manufacture.

Although most nip roller dispensers in the prior art have been employed for dispensing web materials such as paper towels, tickets, and the like, such structure has also been used for dispensing thread-like materials. The British patent to Anderson, No. 21,966 of 1895, for example, discloses a twine holder in which the nip rollers are provided with ratchet means to hold the twine in position for cutting. The device does not provide for control of the amount of twine required.

The U.S. patent to Feinbergh, No. 5,020,554 of Jun. 4, 1991 discloses a combined dental floss dispenser and applicator in which the segment of floss in use is supported between the ends of a bow and tensioned by a pair of nip rollers. However, no means is provided for severing individual lengths of the floss.

SUMMARY OF THE INVENTION

Briefly stated, the invention contemplates the provision of an improved dental floss dispenser which may be mounted upon a bathroom wall adjacent a sink or mirror which may be operated by a single hand of the user to dispense a desired length of floss and sever the same from a self-contained cartridge supply source. The source can be conveniently replaced as required. The length of a desired segment is determined by the user, and wasting of floss is maintained at a minimum.

To this end, the device comprises a housing, and means for supporting said housing from a vertical surface. Within the housing is a vertically oriented plate or wall supporting a resilient clip for retention of a floss cartridge, and a pair of tensioned rollers engaging a continuous segment of floss to advance the same to an exit opening. A cutting blade is positioned immediately adjacent the opening to allow severing of a desired length of floss required, leaving a short segment projecting through the exit opening. The tensioning of the rollers is accomplished in a simple novel manner which facilitates both manufacture and assembly of the device, as well as manual release for threading. Ideally, the device requires only two synthetic resinous injection moldings, and a minimum of hardware.

BRIEF DESCRIPTION OF THE DRAWINGS

In the drawings, to which reference will be made in the specification, similar reference characters have been employed to designate corresponding parts throughout the several views.

FIG. 1 is a side elevational view of an embodiment of the invention.

FIG. 2 is a front elevational view thereof.

FIG. 5 is a side elevational view thereof showing the side opposite that seen in FIG. 1.

FIG. 6 is a side elevational view as seen from the right hand portion of FIG. 5.

FIG. 7 is a vertical transverse sectional view as seen from the plane 7—7 in FIG. 1.

FIG. 8 is a horizontal transverse sectional view as seen from the plane 8—8 in FIG. 1.

DETAILED DESCRIPTION OF THE DISCLOSED EMBODIMENT

Figure 3:
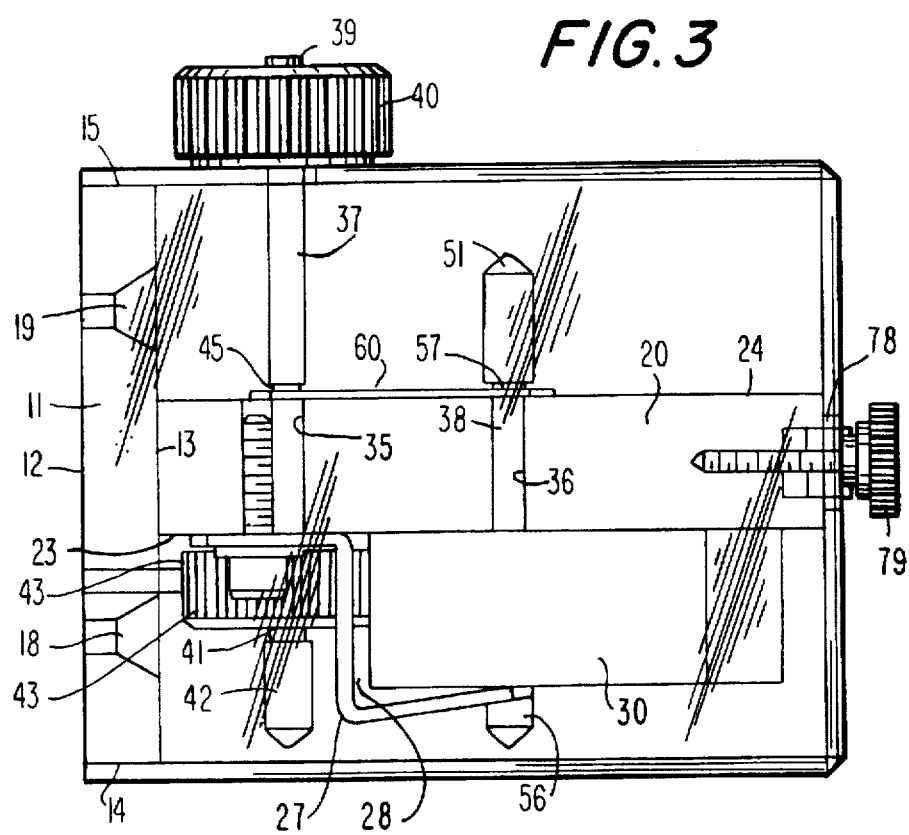
FIG. 3 is a top plan view thereof.
Figure 4:
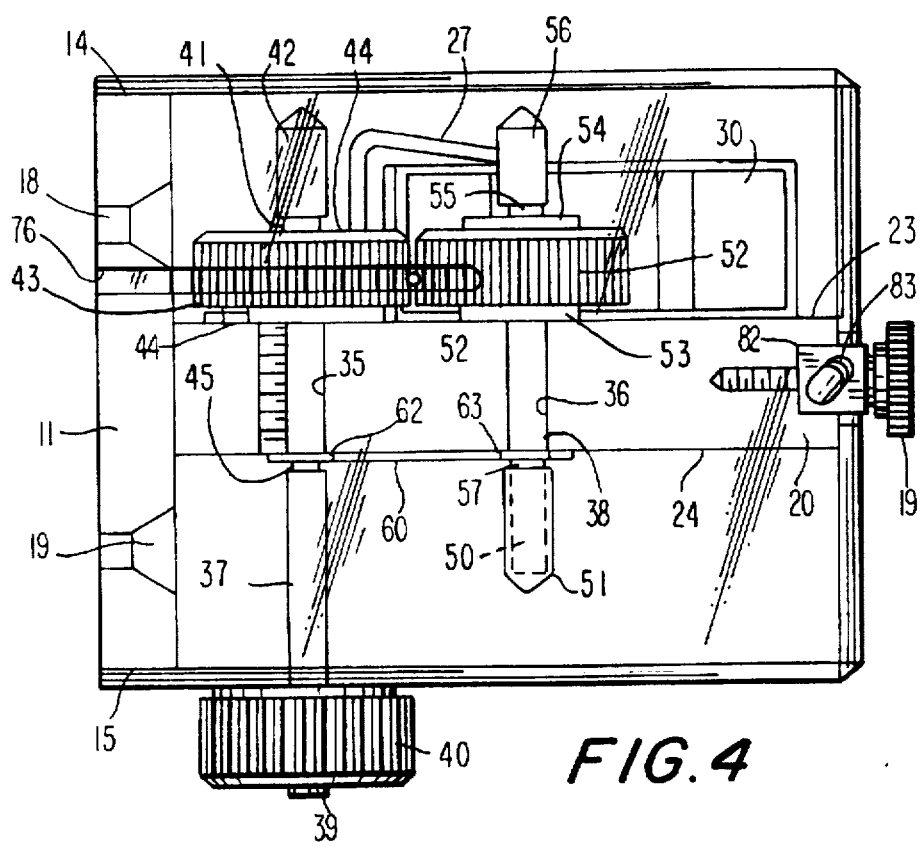
FIG. 4 is a bottom plan view thereof.

In accordance with the first embodiment of the invention, the device, generally indicated by reference character 10 includes a wall-mounted base plate 11 bounded by an outer surface 12, an inner surface 13, side edge surfaces 14 and 15, an upper edge surface 16 and a lower edge surface 17. Two mounting holes 18 and 19 provide for screws (not shown) to secure the plate to a vertical surface.

Projecting perpendicularly from the inner surface 13 is an integrally molded planar wall or septum 20 of substantial thickness, and bounded by an upper surface 21, a lower surface 22, a first side surface 23, and a second side surface 24. Referring to FIGS. 1 and 3, the first side surface 23 mounts a resilient clip 27 forming a recess 28. It is adapted to retain a known dental floss dispenser 30 of pocket-sized configuration in inverted position. One wall 31 includes an opening 32 through which a continuous segment 33 of dental floss projects.

Disposed below the recess 28 are first and second parallel bores 35 and 36 which support a first driven shaft 37 and a second idler shaft 38. The shaft 37 includes a first end 39 mounting a manually engageable knob 40. A second end 41 is provided with a protective cover 40and mounts a force fitted driven nip roller 43 with accompanying low friction washer 44. An annular groove 45 is located immediately adjacent the surface 24.

The shaft 38 includes a first end 50 mounting a protective cover 51 and loosely supports an idler nip roller 52 with accompanying low friction washer 53. It is maintained in position by a retaining washer 54. A second end 55 thereof is also provided with a protective cover 56. An annular groove 57 lies in co-planar relation with the groove 45. The shaft 38 is relatively loosely fitted so that it is capable of lateral, as well as rotational movement. Engaging the grooves 45 and 57 is a piano wire spring 60 including a loop portion 61 and first and second ends 62 and 63 of curvate shape enabling them to be snapped into engagement with the grooves 45 and 57 in such manner as to urge the shafts 37 and 38 away from each other on one side of the wall 20. This has the effect of urging the opposite ends of the shafts which support the nip rollers toward each other in a resilient manner. When it is desired to thread a segment of dental floss therebetween, it is necessary only for the user to engage the protective cover on the first end of one of the shafts and move it in a direction away from the first end of the other shaft against the action of the spring 60 while inserting the segment of floss into the interstice thereby formed. Upon release, the nip rollers will be urged into contact with each other so that rotation will advance the floss upon rotation of the knob 40.

Surrounding the base plate 11 and wall 20 is a housing element 70 including an upper wall 71, a lower wall 72, side walls 73 and 74, and an end wall 75. The lower wall 72 is provided with an elongated slot 76 for the passage of floss. The side wall 74 is provided with an elongated slot 77 for passage of the shaft 38. The end wall 75 includes a centrally disposed orifice 78 through which a retaining screw 79 engages a corresponding threaded bore in an edge surface 25. Adjacent a lower edge 80 is an elongate opening 81 accommodating a small clip 82 having a floss cutting knife edge 83 thereon.

Operation of the device will be apparent from a consideration of the drawings. The user rotates the knob 40 causing the nip rollers 43 and 52 to advance a continuous segment of floss until a desired length is exposed beneath the housing element 70. At this point, the user grasps the segment and moves it into engagement with the knife 83 to sever the same for use. When the cartridge 30 is exhausted, the housing element 70 is removed, a fresh cartridge inserted, and a fresh segment of floss is threaded through the nip rollers in the above-described manner. The housing is then replaced and the operation is continued.

Preferably, substantially the entire device is formed from synthetic resinous injection molded materials, thereby permitting a very reasonable cost of manufacture. By wall-mounting the device, it is not readily misplaced, notwithstanding its relatively small size, and only the fingers of a single hand are required for operation. In the disclosed embodiment, the device is formed from transparent materials. However, where desired, opaque materials may alternatively be used.

I wish it to be understood that I do not consider the invention to be limited to the precise details of structure shown and set forth in the specification, for obvious modifications will occur to those skilled in the art to which the invention pertains.

I claim:

1. A dental floss dispenser comprising: a generally planar base plate having means for mounting upon a vertical surface against a first surface of said base plate, said base plate having an oppositely disposed second surface, a wall extending perpendicularly from said second surface, said wall supporting a resilient means defining a recess for retaining a supply of dental floss, said wall having a vertical surface extending parallel to a surface of said recess; floss segment guiding means positioned beneath said recess; said wall defining first and second parallel bores, a first shaft radially loosely fitted within said first bore having first and second ends, a first nip roller fitted upon said first end of said first shaft for free rotation relative thereto, means for retaining said nip roller on said shaft; a second shaft radially loosely fitted for rotation within said second bore having first and second ends, a second nip roller force-fitted to said second shaft at said first end thereof, said first and second nip rollers being on a first side of said wall a manually engageable knob fitted to said second end of said second shaft; and a looped spring having a first end engaging said first shaft on a second side of said wall opposite said first side, and a second end engaging said second shaft on said second side of said wall to urge the first and second shafts apart on said second side of said wall and urge said nip rollers on said first side of said wall into mutual engagement.

2. A dental floss dispenser in accordance with claim 1, further comprising a housing element engaging said base plate and said wall, said housing element defining an opening for the passage of a continuous segment of floss therethrough, and knife means for severing said segment of floss positioned adjacent said opening.

3. A dental floss dispenser in accordance with claim 2, said housing defining a second opening for passage of said second shaft therethru, said manually engageble knob being mounted on said second shaft exterioly of said housing.

* * * * *